United States Patent [19]
Uehara

[11] Patent Number: 5,472,715
[45] Date of Patent: Dec. 5, 1995

[54] ANTIFUNGAL AGENT FOR THE TREATMENT OF SKIN DISEASE CAUSED BY TRICHOPHYTON, ECZEMA OR VARIOUS FUNGI, AND ALSO FOR ACTIVATING THE RECOVERY OF THE SKIN AND BURNS

[75] Inventor: Kazutoyo Uehara, Zama, Japan

[73] Assignee: Japan Lotion Company, Kanagawa, Japan

[21] Appl. No.: 365,815

[22] Filed: Dec. 29, 1994

Related U.S. Application Data

[63] Continuation of Ser. No. 165,645, Dec. 13, 1993.

[30] Foreign Application Priority Data

Dec. 11, 1992 [JP] Japan ................... 4-359717

[51] Int. Cl.$^6$ .................. A61K 33/00; A61K 33/20; A61K 33/40
[52] U.S. Cl. ............... 424/613; 424/616; 424/661; 424/662; 424/711; 424/718
[58] Field of Search .................. 424/613, 616, 424/661, 662, 711, 718

[56] References Cited

U.S. PATENT DOCUMENTS

| | | | |
|---|---|---|---|
| 2,745,407 | 5/1956 | Mueller et al. | 128/407 |
| 4,097,395 | 6/1978 | Posey et al. | 252/106 |
| 4,164,477 | 8/1979 | Whitley | 252/99 |
| 4,375,812 | 3/1983 | Vaseen et al. | 128/207.27 |
| 4,518,585 | 5/1985 | Greene et al. | 424/130 |
| 4,737,307 | 4/1988 | Brown et al. | 252/106 |
| 5,098,415 | 3/1992 | Levin | 604/293 |
| 5,270,344 | 12/1993 | Herman | 514/725 |

*Primary Examiner*—Shep Rose
*Attorney, Agent, or Firm*—Wenderoth, Lind & Ponack

[57] ABSTRACT

An antifungal agent for the treatment of skin disease such as athlete's foot, ringworm and tinea caused by dermatophytes, eczema, tinea or various fungi, which comprises a 100 weight % of detergent solution including 0.01–40 weight % of sodium hypochlorite, 0.01–30 weight % of sodium sulfite, 0.01–40 weight % of sodium nitrite, 0.01–40 weight % of sodium chlorate, 0.01–40 weight % of potassium chlorate, 0.001–35 weight % of hydrogen peroxide, 0.01–40 weight % of ozone water, 0.01–40 weight % of sodium nitrite, 0.01–40 weight % of potassium nitrite, 0.001–1 weight % of nonionic surface active agent and 1–90 weight % of water.

It is characterized in that trichophyton, eczema or various fungi in the dermis or deep layer are allured by oxygen contained in the antifungal agent to or near the surface of the skin for easy sterilization by oxidation, reduction, bleaching and fungicidal activity.

A liquid agent is also efficacious for the treatment of a burn of the skin and of stiffness in the shoulders.

4 Claims, No Drawings

ANTIFUNGAL AGENT FOR THE TREATMENT OF SKIN DISEASE CAUSED BY TRICHOPHYTON, ECZEMA OR VARIOUS FUNGI, AND ALSO FOR ACTIVATING THE RECOVERY OF THE SKIN AND BURNS

This is a continuation application of Ser. No. 08/165,645, filed Dec. 13, 1993.

BACKGROUND OF INVENTION

1. Field of the Invention

This invention relates to an antifungal agent for the treatment of skin disease (infecticosa eczematoides or Engmaris disease) caused by trichophyton, eczema or various fungi, and also for activating the recovery of the skin disease and burns.

More particularly, this invention relates to an antifungal agent for the treatment of skin disease such as athlete's foot, ringworm and tinea by oxidation, reduction, bleaching and fungicidal activity of the antifungal agent, which is characterized in that trichophytons or various fungi in a deep layer of the skin are allured by oxygen contained in the antifungal agent to or near the surface of the skin for easy sterilization, and also for activating the early recovery of the skin diseases and burns.

2. Description of the Prior Art

In case trichophyton causing athlete's foot or ringworm are in the epidermis of the skin, it is comparatively easy to sterilize them. When they are in a deep layer such as keratin or dermis of the skin, complete sterilization of trichophytons cannot be expected, thus leaving the skin disease beyond medical treatment.

Some antifungal agents containing econazole nitrate, phydone derivative or miconazole nitrate for the remedy of athlete's foot and ringworm have been proposed in, which keratin or the epidermis and the dermis of the skin are corroded by another medicine.

Since the healthy skin is also corroded, the early recovery of the skin affected with dermatotophytoses, eczema or various fungi cannot be expected.

Another conventional antifungal agent containing fluoride for the remedy of athlete's foot or ringworm has also been proposed, but fluoride not only sterilizes trichophyton, but also corrodes the healthy epidermis, dermis and deep skin and even the bone as well.

SUMMARY OF THE INVENTION

A principal object of this invention is to provide an antifungal agent for the treatment of skin disease such as athlete's foot, ringworm and tinea by oxidation, reduction, bleaching and fungicidal activity of the antifungal agent, which is characterized in that trichophyton or various fungi in a deep layer of the skin are allured by oxygen contained in the antifungal agent to or near the surface of the skin for easy and early sterilization.

Another object of this invention is to provide an antifungal agent for activating the recovery of skin disease (infection eczematoides or Engmaris disease) causes by trichophyton, eczema or various fungi which is characterized in that oxygen contained in the antifungal agent plays an important role in the recovery of the affected skin or a burn of the skin.

Another object of this invention is to provide an antifungal agent for the treatment of skin diseases such as athlete's foot, ringworm and tinea in a safe and economic manner.

A further object of this invention is to provide a liquid agent (or lotion) for the treatment of a burn of the skin.

Still another object of this invention is not provide a liquid agent (or lotion) for the treatment of stiffness in the shoulders.

ESSENTIAL FEATURE OF THE INVENTION

An antifungal solution for the treatment of the skin diseases such as athlete's foot, ringworm and tinea of this invention comprises sodium hypochlorite, sodium sulfite, sodium nitrite, sodium chlorate, potassium chlorate, hydrogen peroxide, ozone water, sodium nitrate, potassium nitrate, nonionic surface active agent and water, and it is characterized in that trichophyton or various fungi in a deep layer of the skin are allured by oxygen contained in the antifungal agent to or near the surface of the skin for easy sterilization and also for activating the early recovery of the skin affected with dermatophytes, eczema or various fungi by oxidation, reduction, bleaching and fungicidal activity of the antifungal solution, and that the skin affected with the dermatophytes, eczema or various fungi can be recovered quite easily and early.

EXAMPLES

Example 1

A detergent solution of an antifungal agent for the treatment of skin diseases caused by trichophyton and eczema of this invention comprises a 100 weight % solution including 0.01–40 weight % of sodium hypochlorite, 0.01–30 weight % of sodium sulfite, 0.01–40 weight % of sodium nitrite, 0.01–40 weight % of sodium chlorate, 0.01–40 weight % of potassium chlorate, 0.001–35 weight % of hydrogen peroxide, 0.01–40 weight % of ozone water, 0.01–40 weight % of sodium nitrate, 0.01–40 weight % of potassium nitrate, 0.001–1 weight % of non-ionic surface active agent and 1–90 weight % water.

Example 2

A detergent solution of the antifungal agent for the treatment of skin diseases caused by trichiphyton and eczema described in Example 1 has pH value between 4–12.

Example 3

The detergent solution of the antifungal agent was adjusted to have the pH value of 12. The adjusted solution was applied once a day to the flaky, oozy and cracked skin on the sole of a foot of 48 year old man. After three days of its application, the trichophyton was completely sterilized, taking away not only usual urtication of the athlete's foot, but also urtication felt when the body temperature of the patient rises.

At the same time, the skin affected with the athlete's foot recovered quite earlier than the case treated with the conventional remedy for athlete's foot.

Example 4

The aforementioned solution was applied once a day to eczema on the instep of a foot and on the back of a hand of a 55 year old woman, curing her of the diseases completely after about 3 days.

Example 5

The aforementioned solution was applied once a day to dermatophyte and eczema of a toenail of a 55 year old man, and cured him of the diseases completely after about 10 days.

Example 6

The aforementioned solution was applied once a day to dermatophyte on the palm of a man 43 years old, and cured him of the disease completely after about 3 days.

Example 7

A cotton patch soaked with the aforementioned solution was applied at night on both shoulders of a 57 year old man who had been suffering from chronic stiffness in the shoulders, and facilitated the circulation of the blood to cure him of his chronic stiffness the next morning.

Example 8

A 54 year old woman burnt her left hand near the thumb for 3 square cm area while frying "Tempura" (or Japanese deep-fat fried food). She had applied on the burn the aforementioned solution soaked in a cotton patch for one week to cure her of the burn completely.

In accordance with the antifungal agent of this invention, it is characterized in that trichophytons or various other fungi in a deep layer of the skin are allured by oxygen contained in the antifungal agent to or near the surface of the skin for easy and early sterilization and also for activating the early recovery of the skin affected with the aforementioned diseases and burns.

Although the foregoing invention has been described in some detail by way of illustration and example for purposes of clarity of understanding, it will be obvious that certain changes and modifications may be practiced within the scope of the appended claims.

What is claimed is:

1. An antifungal agent for the treatment of skin disease which comprises:

a 100 weight % of detergent solution including 0.01–40 weight % of sodium hypochlorite, 0.01–30 weight % of sodium sulfite, 0.01–40 weight % of sodium nitrite, 0.01–40 weight % of sodium chlorate, 0.01–40 weight % of potassium chlorate, 0.001–35 weight % of hydrogen peroxide, 0.01–40 weight % of ozone water, 0.01–40 weight % of sodium nitrate, 0.01–40 weight % of potassium nitrate, 0.001–1 weight % of nonionic surface active agent and 1–90 weight % of water.

2. An antifungal agent as claimed in claim 1, which is an antifungal detergent solution having a pH value between 4–12.

3. An antifungal detergent solution as claimed in claim 1 which comprises:

a 100 weight % of detergent solution including 0.01–40 weight % of sodium hypochlorite.

4. An antifungal detergent solution as claimed in claim 2 which comprises:

a 100 weight % of detergent solution including 0.01–40 weight % of sodium hypochlorite.

* * * * *